US010076303B2

(12) United States Patent
Medan et al.

(10) Patent No.: US 10,076,303 B2
(45) Date of Patent: Sep. 18, 2018

(54) MOTION COMPENSATION FOR NON-INVASIVE TREATMENT THERAPIES

(75) Inventors: Yoav Medan, Haifa (IL); Kobi Vortman, Haifa (IL)

(73) Assignee: INSIGHTEC, LTD., Tirat Carmel (IL)

( * ) Notice: Subject to any disclaimer, the term of this patent is extended or adjusted under 35 U.S.C. 154(b) by 493 days.

(21) Appl. No.: 13/226,060

(22) Filed: Sep. 6, 2011

(65) Prior Publication Data
US 2012/0059243 A1 Mar. 8, 2012

Related U.S. Application Data

(60) Provisional application No. 61/380,487, filed on Sep. 7, 2010.

(51) Int. Cl.
| | |
|---|---|
| A61B 5/05 | (2006.01) |
| A61B 8/08 | (2006.01) |
| A61N 7/02 | (2006.01) |
| A61B 5/055 | (2006.01) |
| A61B 5/113 | (2006.01) |
| A61B 5/00 | (2006.01) |
| A61B 90/00 | (2016.01) |

(52) U.S. Cl.
CPC .......... *A61B 8/08* (2013.01); *A61N 7/02* (2013.01); *A61B 5/055* (2013.01); *A61B 5/1135* (2013.01); *A61B 5/6831* (2013.01); *A61B 2090/374* (2016.02); *A61B 2090/378* (2016.02)

(58) Field of Classification Search
CPC ............ A61B 8/145; A61B 5/11; A61B 5/005
USPC .................................................. 600/407–480
See application file for complete search history.

(56) References Cited

U.S. PATENT DOCUMENTS

| | | | | |
|---|---|---|---|---|
| 4,009,393 | A * | 2/1977 | Ashley et al. | 250/339.05 |
| 5,365,603 | A * | 11/1994 | Karmann | 382/291 |
| 5,629,967 | A | 5/1997 | Leksell et al. | |
| 5,946,425 | A | 8/1999 | Bove, Jr. et al. | |
| 6,228,030 | B1 * | 5/2001 | Urbano et al. | 600/443 |
| 6,804,548 | B2 | 10/2004 | Takahashi et al. | |
| 6,970,585 | B1 * | 11/2005 | Dafni et al. | 382/131 |
| 8,874,187 | B2 * | 10/2014 | Thomson et al. | 600/407 |
| 2002/0077545 | A1 | 6/2002 | Takahashi et al. | |
| 2003/0125622 | A1 * | 7/2003 | Schweikard et al. | 600/437 |
| 2005/0030024 | A1 | 2/2005 | Golay et al. | |
| 2005/0152495 | A1 | 7/2005 | Hesse | |
| 2005/0197564 | A1 | 9/2005 | Dempsey | |
| 2005/0251029 | A1 | 11/2005 | Khamene et al. | |
| 2006/0002630 | A1 | 1/2006 | Fu et al. | |
| 2006/0036156 | A1 | 2/2006 | Lachaine et al. | |
| 2006/0241332 | A1 | 10/2006 | Klein et al. | |
| 2006/0293584 | A1 * | 12/2006 | Kojima et al. | 600/407 |
| 2007/0092110 | A1 * | 4/2007 | Xu | G06T 7/2033 382/103 |
| 2007/0167739 | A1 * | 7/2007 | Salo | A61B 8/0833 600/424 |
| 2008/0002811 | A1 | 1/2008 | Allison | |
| 2008/0049896 | A1 | 2/2008 | Kuduvalli | |
| 2008/0071131 | A1 | 3/2008 | Rietzel | |
| 2008/0081991 | A1 | 4/2008 | West et al. | |
| 2008/0219406 | A1 | 9/2008 | Kaus et al. | |
| 2009/0088623 | A1 | 4/2009 | Vortman et al. | |
| 2009/0124893 | A1 | 5/2009 | Schlaefer | |
| 2009/0147916 | A1 | 6/2009 | Fallone et al. | |
| 2010/0198101 | A1 * | 8/2010 | Song et al. | 600/547 |
| 2011/0109796 | A1 | 5/2011 | Subedar et al. | |
| 2012/0029396 | A1 | 2/2012 | Vortman et al. | |

FOREIGN PATENT DOCUMENTS

| | | |
|---|---|---|
| WO | WO-02/072190 | 9/2002 |
| WO | 2007/084272 A1 | 7/2007 |

OTHER PUBLICATIONS

International Application Serial No. PCT/IB2011/002117, International Search Report and Written Opinion dated Jan. 17, 2012, 10 pages.
International Application Serial No. PCT/IB2011/002117, International Preliminary Report on Patentability, dated Feb. 7, 2013, 8 pages.

* cited by examiner

*Primary Examiner* — James Kish
*Assistant Examiner* — Vani Gupta
(74) *Attorney, Agent, or Firm* — Morgan, Lewis & Bockius LLP

(57) ABSTRACT

Procedures and systems facilitate non-invasive, focused delivery of therapeutic energy to a target within or on a patient using, in various embodiments, a closed-loop approach such that feedback regarding anatomical movement and/or morphology changes is tracked and the uncertainty inherent in the measurements is addressed.

12 Claims, No Drawings

MOTION COMPENSATION FOR NON-INVASIVE TREATMENT THERAPIES

RELATED APPLICATION

This application claims priority to, and the benefits of, U.S. Ser. No. 61/380,487, filed on Sep. 7, 2010, the entire disclosure of which is hereby incorporated by reference.

TECHNICAL FIELD

The present invention relates generally to systems and methods for performing noninvasive procedures using acoustic energy, and, more particularly, to systems and methods for focusing and adjusting the delivery of ultrasonic energy during treatment.

BACKGROUND INFORMATION

Tissue, such as a benign or malignant tumor, organ, or other body region may be treated invasively by surgically removing the tissue, with minimal invasion or non-invasively by using, for example, thermal ablation. Both approaches may effectively treat certain localized conditions, but involve delicate procedures to avoid destroying or damaging otherwise healthy tissue.

Thermal ablation, as may be accomplished using focused ultrasound, has particular appeal for treating diseased tissue surrounded by or neighboring healthy tissue or organs because the effects of ultrasound energy can be confined to a well-defined target region. Ultrasonic energy may be focused to a zone having a cross-section of only a few millimeters due to relatively short wavelengths (e.g., as small as 1.5 millimeters (mm) in cross-section at one Megahertz (1 MHz)). Moreover, because acoustic energy generally penetrates well through soft tissues, intervening anatomy often does not impose an obstacle to defining a desired focal zone. Thus, ultrasonic energy may be focused at a small target in order to ablate diseased tissue while minimizing damage to surrounding healthy tissue.

To focus ultrasonic energy toward a desired target, drive signals may be sent to an acoustic (preferably piezoelectric) transducer having a number of transducer elements such that constructive interference occurs at the focal zone. At the target, sufficient acoustic energy may be delivered to heat tissue until necrosis occurs, i.e., until the tissue is destroyed. Preferably, tissue along the path through which the acoustic energy passes (the "pass zone") outside the focal zone is heated only minimally, if at all, thereby minimizing damage to tissue outside the focal zone.

Typically, ultrasonic energy is delivered according to a treatment plan, often based on a predefined model of the target and the patient's anatomy. However, because the human body is flexible and certain organs move (due to breathing, for example), treatment delivered as multiple sonications over time (even when delivered within seconds of each other) may require interim adjustments to targeting and/or to one or more treatment parameters to compensate for movement of the target. Indeed, absorption of ultrasound energy may itself change the shape and/or location of the target through swelling, for example, necessitating similar changes. This creates a significant challenge given the need to avoid damage to healthy tissue while still achieving complete ablation of the target.

One approach for tracking a moving anatomical target uses an imaging device to capture periodic images of the target and compare the target's location in the image to the treatment plan. In such cases, clearly visible landmarks of the target (or organ in which the target is located) may be used to identify the target within every imaging frame. However, the intra-frame motion of the target may lead to substantial targeting inaccuracy. This uncertainty is further compounded by any computational lags associated with capturing and analyzing the imaging data. Typically, the more accurate the image, the more computationally intensive the image processing becomes, resulting in a longer latency—meaning there is an inherent uncertainty about the actual location of the target at the point in time when the data is actually available to be viewed and/or acted upon.

Accordingly, there is a need for systems and methods for effectively focusing acoustic energy in a manner that does not adversely affect surrounding tissue and can be administered in a timely fashion while considering movement of both the target and the surrounding tissue.

SUMMARY OF THE INVENTION

The present invention provides procedures and systems that facilitate non-invasive, focused delivery of therapeutic energy to a target within or on a patient. In general, the technique uses a closed-loop approach such that feedback regarding anatomical movement and/or morphology changes is tracked and the uncertainty inherent in the measurements is addressed. To address this uncertainty and the need to steer or aim the energy remains on the target while the target is in motion, an image content based tracking technique is used with motion-vector prediction based on a physical model or estimation of the target motion characteristics. Fast-rate information sources (e.g., those that have been optimized based on rate of data capture and processing at the expense of other factors such as spatial resolution, volume, signal-to-noise ratio, etc.) may be introduced into the tracking loop in order to further limit the uncertainty. Such high-rate sources exhibit smaller latency and therefore reduce the uncertainty of the target location and confirm the validity (or guide adjustment) of the prediction model used to plan the treatment regimen.

In a first aspect, a method of monitoring movement of a target volume of tissue during treatment of the volume includes obtaining a model of the anticipated movement of the volume and tracking the volume during treatment. The tracking is done using periodic imaging and/or measurements using two different tracking modalities, each having a different sampling frequency. A first tracking modality provides estimated target locations based on surrogate measurements at a fast frequency and short latency (20 Hz, for example), while the second modality provides actual target locations at a second, lower frequency and higher latency (e.g., 2-10 Hz) and with higher spatial resolution. As estimated locations are received, they are compared to the model to determine a tracking error. The tracking error may then be compared to a safety threshold and, if the threshold is exceeded, the treatment is suspended. The actual locations of the volume may be used to update treatment tracking model parameters as the treatment progresses.

The model to which the estimated (and in some cases actual) locations are compared may be a vector prediction model that predicts the location of the target volume as a function of time and an initial (or previously observed) location. The estimated and/or actual observed locations may be used to update the model. The first and/or second tracking loops may be adjusted during treatment based on the target dynamics (e.g., movement, morphing, etc.), the tracking error, or both. The treatment being delivered to the target may include or consist of focused ultrasound, in which case the treatment parameters may include a beam intensity, beam location, focal point, beam angle, as well as other beam steering and temporal data.

In another aspect, a system for monitoring movement of a volume of tissue to facilitate treatment of the volume includes a register for storing a model describing the anticipated movement or morphing of the target volume between actual measurements of its location over time and as it is subjected to treatment. The register also stores representations of estimated target locations obtained using a first detection modality operating at a particular frequency (e.g., approximately 15-30 Hz), and representations of actual target locations obtained using a different detection modality operating at a second, slower frequency (approximately 2-5 Hz). A processor compares the estimated target locations to the model to determine an estimated tracking error and determines if the tracking error exceeds a safety threshold. If so, a controller instructs or causes a treatment device to suspend treatment.

In some implementations, the detection modalities comprise imaging devices such as a magnetic resonance imaging device (MRI), a one-, two- or three-dimensional ultrasound device or a fast electro-optics tracking device (e.g., cameras). The estimated target volume locations may be measured directly or indirectly, and obtained using a surrogate device such as a respiratory belt, or an optical tracking device using lasers or infrared beams and reflective fiducials attached to the patient. A vector prediction model may provide the anticipated target movement based on a known initial target location, interim target locations and/or movement models associated with breathing or organ displacement.

The actual volume locations may be used to update the prediction model, update treatment parameters, or both. The updated treatment parameters may be implemented after treatment is suspended, or, in some cases during treatment delivery. Treatment parameters may include beam intensity, beam location, focal point, beam angle, as well as other beam steering and temporal data.

The foregoing and other objects, features and advantages of the present invention disclosed herein, as well as the invention itself, will be more fully understood from the following description of preferred embodiments and claims, when read together with the accompanying drawings.

DETAILED DESCRIPTION

Conventional techniques for tracking an anatomical target via imaging involve placement or selection of visible landmarks on or in the target lesion or organ, and, using various imaging techniques, identifying the target on each image frame; see, e.g., U.S. Ser. No. 13/194,286, filed on Jul. 29, 2011, and U.S. Ser. No. 11/865,662, filed on Oct. 1, 2007, the entire disclosures of which are hereby incorporated by reference. Using this technique, the image-acquisition rate relative to the organ motion velocity determines the accuracy or uncertainty of the target location. The uncertainty may be compounded by computational lags associated with capturing and analyzing the imaging data. This uncertainty and the need to adjust the path of the acoustic beam in order to keep the focal spot on the target presents a particular challenge for healthcare providers as they deliver ultrasound or other focused therapy to a patient. Typically, the more accurate the tracking modality, the more computationally intensive the processing becomes, hence increasing latency. Therefore, the process may result in an accurate location, but that location may be erroneous or misleading by the time the energy is actually delivered.

In accordance with various embodiments of the present invention, a system for tracking the movement of tissue uses two separate measurement modalities to determine the location of the tissue. Each modality provides a distinct feedback loop to determine the location of the target, and to guide or halt treatment of the target using a focused ultrasound device. While the examples herein describe the technique with respect to the delivery of ultrasound energy, it should be understood that these same systems and methods may be applied to the delivery of other therapeutic modalities, such as radiation therapy, image-guided surgery, and others. The two modalities operate at different information update rates and have different post-capture processing requirements. A "fast tracking loop" uses data that is either readily available (e.g., target movement based on a predetermined model, as described in U.S. Ser. No. 12/615,780, filed on Nov. 10, 2009, the entire disclosure of which is hereby incorporated by reference, or obtained with very low latency (e.g., gross measurements without complex post-processing requirements or with limited resolution) to influence treatment parameters. In one embodiment, the fast tracking loop uses a pre-programmed target path as a surrogate for (i.e., an estimate of) the location of the target during a treatment regimen. While the fast tracking loop can direct the treatment in near real time due to its low latency, the data it relies on may be imperfect, and over time the accuracy may decrease. In some cases, the accuracy may decrease to a point at which treatment must be stopped completely and tracking recalibrated.

In conjunction with the fast tracking loop, a "slow loop" is used to determine the actual location of the target at a given time. Because the slow loop typically has a higher latency due to the complexity of capturing, processing and storing the data, relying solely of the slow loop to determine treatment parameters can introduce unwanted errors. In some embodiments, the slow loop modality may also be used to derive an initial training model to obtain nominal or average parameters before the actual treatment starts. These parameters may be used in conjunction with the fast loop tracking model to enhance the accuracy of the model.

However, augmenting the fast loop tracking data with slow loop location data allows target tracking to occur during treatment while minimizing the uncertainties created by latency. As a result, the accuracy of the fast tracking loop model used to estimate the targets location can be checked on a periodic basis. While the fast loop tracking information may not provide a direct measurement of the target location (or may do so but with limited resolution), it maintains one or more surrogate parameters that have a high correlation to the actual target location, as well as target velocity and direction information (motion vector), which may serve as input into the location prediction model used to steer the acoustic beam. An ultrasound imaging sensor, a respiration belt, fast one-dimensional magnetic resonance scans such as ARFI, a Tmap pencil beam, RF tagging or a navigator pulse, as well as other sensors may be used as high-rate sources; see, e.g., U.S. Ser. No. 12/769,059, filed on Apr. 28, 2010, the entire disclosure of which is hereby incorporated by reference. Slow-loop imaging modalities such as MRI can provide high-resolution, accurate anatomical location data, albeit with a significant delay.

If, for example, using the fast loop tracking modality, a determination is made that a safety threshold has been exceed (e.g., the difference between the predicted location and the actual location is above a threshold) due to excessive target velocity or any other error source, delivery of energy to the target can be halted until more accurate and dependable location information can be obtained using the slow loop, latent imaging process.

Alternatively, the path of the acoustic beam may be altered by re-steering the beam towards the correct target and/or by updating predictor parameters in the model in order to account for the observed deviation. The steering correction may be implemented periodically or, in some cases, on demand. When done on demand, the re-steering may occur asynchronously depending on the distance between the focal spot and the target. When the distance exceeds a certain threshold, the beam is "instantaneously" steered to the correct location. In general, "instantaneous" steering refers to the substantially immediate correction obtainable through electronic corrections to beam phase or similarly rapid mechanical adjustments, as opposed to the longer times necessary to mechanically correct the position and orientation of a transducer.

One approach to updating the predictor model is to use a Kalman filter. This approach employs the movement model, known control inputs, and, optionally, sensor measurements to estimate the "state" of the beam relative to the target. Using the Kalman filter, the current state (or a series of previous states) is combined with a new measurement to alter the model based on a revised state. In some embodiments, a weighted average may be used to account for a higher confidence in certain states (e.g., more recent states or states measured using more than one sensor) than others. The weights may be calculated based on the estimated uncertainty of the predictions of the target state. The result of the weighted average is a new state estimate that lies between the predicted and measured states, and has a better estimated uncertainty than either alone. This process may be repeated for successive time increments, with the new estimate and its covariance informing the prediction used in the following iteration.

In this example, the system operates in two distinct phases: a prediction phase and an update phase. In the prediction phase, the target's old position is updated according to a stored vector prediction model based on known attributes of the target and physical laws of motion to provide a "dead reckoning" estimate of the lesion's location. In the update phase, a measurement of the target's actual position is obtained using a more accurate (but computationally more burdensome) imaging process, effectively providing a measurement of the exact location of the target. Ideally, as the dead reckoning estimates drift away from the actual position, the more accurate measurement resets the location to the real position.

In another implementation, the fast-loop and slow-loop tracking may be accomplished using the same (or similar) image data obtained at different resolutions and frequencies. Specifically, the slow-tracking loop may have a high spatial resolution such that every point or voxel within the target is tracked. In one particular example, the slow-tracking loop may track 500,000 voxels with a frequency of 1 Hz. The fast-tracking loop, which may use the same imaging modality, may only be able to track 50,000 voxels but do so with a frequency of 10 Hz.

Using these two tracking methods to monitor an organ moving non-cyclically at 10 mm/sec, the error in the slow-tracking data could be as high as 10 mm. However, combining the two tracking loops data minimizes the error. For example, the fast-tracking loop may be used to monitor a set of voxels that are "evenly dispersed" throughout the larger tracked volume and assume that around each tracked voxel a neighborhood of ~10 voxels behaves in the same manner as the tracked voxel.

In other implementation, the latency and acquisition averaging of the slow-tracking loop may be used. For example, using the slow-tracking loop (with a latency of 0.5 seconds), location data for 500,000 voxels can be averaged during acquisition over a 0.5 second period. Substantially simultaneously, the fast tracking loop may be used to collect location data having a latency of 0.75. The two sets of data may then be compared and used to develop a transformation matrix for the whole volume, or sub-volumes if the motion is non rigid. Each time a comparison is made between the fast loop tracked voxels (delayed to take into account latency and averaging) to the relevant subset of the voxels from the slow loop tracker, corrections to the matrix may be made, or, in some cases, treatment terminated.

The methods and techniques describe above may be implemented in hardware and/or software and realized as a system for tracking tissue, lesions, blood vessels, organs or other targets within or on a patient. For example, the system may utilize one or more data registers to store the slow loop track image data, the fast loop track surrogate data, and the vector-based movement models used to track and predict the target(s) locations. The system may also use one or more processors and/or use portions of a computer's random access memory to provide control logic that implements the tracking and correction techniques described above. In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software could be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, computer-readable program means such as a floppy disk, a hard disk, an optical disk, a magnetic tape, a PROM, an EPROM, one or more FGPAs, graphics accelerator boards, firmware, or CD-ROM.

While the invention has been particularly shown and described with reference to specific embodiments, it should be understood by those skilled in the area that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A method of continuously monitoring movement of an internal volume of tissue during treatment thereof, the method comprising the steps of:
   using a physical model of anticipated movement of an internal target volume to predict a target volume location as a function of time;
   continuously and directly tracking the internal target volume during treatment thereof using two tracking modalities, wherein the first tracking modality provides initial estimated target volume locations based directly on first image contents of the internal target volume obtained at a first information update rate, and the second tracking modality identifies subsequent estimated target locations of the internal target volume based directly on second image contents of the internal target volume obtained at a second information update rate lower than the first information update rate wherein the subsequent estimated target locations are more accurate than the initial estimated target volume locations;

comparing the initial estimated target volume locations to the predicted target volume locations to determine a tracking error;

if the tracking error exceeds a safety threshold, suspending treatment; and adjusting one or more parameters of the physical model based on the subsequent estimated target volume locations of the target volume.

2. The method of claim 1 wherein the physical model comprises a vector prediction model.

3. The method of claim 1 wherein the first update rate is above 10 Hz and the second update rate is below 10 Hz.

4. The method of claim 1 further comprising adjusting at least one of the first or second information update rates based at least in part on motion of the target volume as determined from the tracking step.

5. The method of claim 1 wherein the first tracking modality and the second tracking modality comprise imaging devices.

6. The method of claim 1, further comprising using the physical model to steer an acoustic beam.

7. A system for continuously and directly monitoring movement of an internal volume of tissue during treatment thereof, the system comprising:

a register for storing (i) a physical model of anticipated movement of an internal target volume for predicting a target volume location as a function of time, (ii) representations of estimated target volume locations based directly on first image contents of the internal target volume obtained using a first tracking modality at a first information update rate, and (iii) representations of target volume locations based directly on second image contents of the internal target volume obtained using a second tracking modality at a second information update rate lower than the first information update rate;

a processor for (i) comparing the estimated target volume locations to the predicted target volume locations to determine a tracking error, (ii) determining if the tracking error exceeds a safety threshold, and (iii) adjusting one or more parameters of the physical model based on the target volume locations obtained using the second tracking modality; and a controller for suspending treatment to the target if the tracking error exceeds the safety threshold.

8. The system of claim 7 wherein the first tracking modality comprises use of a one-dimensional magnetic resonance imaging device.

9. The system of claim 7 wherein the second tracking modality comprises use of an ultrasound device.

10. The system of claim 7 wherein the physical model comprises a motion vector prediction model.

11. The system of claim 7 wherein the processor adjusts one or more treatment parameters based on the predicted target location determined with the physical model.

12. The system of claim 7 wherein the first information update rate is greater than 10 Hz and the second information update rate is less than 10 Hz.

* * * * *